United States Patent
Wolfe et al.

(10) Patent No.: US 8,716,249 B2
(45) Date of Patent: May 6, 2014

(54) COMPOSITIONS AND METHODS FOR IMPROVING CARDIOVASCULAR HEALTH

(75) Inventors: Robert Wolfe, Little Rock, AR (US); John Troup, Plymouth, MN (US); Nicolaas ("Mick") Emile Paulus Deutz, Little Rock, AR (US)

(73) Assignee: Energy Light LLC, McLean, VA (US)

( * ) Notice: Subject to any disclaimer, the term of this patent is extended or adjusted under 35 U.S.C. 154(b) by 1017 days.

(21) Appl. No.: 12/023,413

(22) Filed: Jan. 31, 2008

(65) Prior Publication Data
US 2009/0197820 A1     Aug. 6, 2009

(51) Int. Cl.
*A61K 31/70* (2006.01)
*A61K 31/56* (2006.01)
*A61P 9/00* (2006.01)

(52) U.S. Cl.
USPC ............. 514/23; 514/171; 536/1.11; 426/656

(58) Field of Classification Search
USPC .................. 514/23, 171; 536/1.11; 426/656
See application file for complete search history.

(56) References Cited

U.S. PATENT DOCUMENTS

| | | |
|---|---|---|
| 2005/0002992 A1 | 1/2005 | McCleary et al. |
| 2005/0106218 A1 | 5/2005 | Ward et al. |
| 2006/0217356 A1* | 9/2006 | Wright et al. ............... 514/171 |
| 2007/0218113 A1* | 9/2007 | Miller et al. ................ 424/439 |
| 2008/0038320 A1 | 2/2008 | Oommen et al. |

FOREIGN PATENT DOCUMENTS

WO     2006116755 A2     11/2006

OTHER PUBLICATIONS

Grasso et al. (Lancet (1968), II (7571), 755-6) (Abstract sent).*
International Search Report, International Application No. PCT/US08/88216, mailed on Aug. 7, 2009, 13 pages.

* cited by examiner

*Primary Examiner* — Shaojia Anna Jiang
*Assistant Examiner* — Michael C Henry
(74) *Attorney, Agent, or Firm* — Carrie Stroup (57) ABSTRACT

Compositions and methods for improving cardiovascular health in the elderly by delivering a selection of essential amino acids, phytosterols, stanols, and isoflavones, which may be supplemented with a low glycemic carbohydrate and/or a medium chain fatty acid.

11 Claims, 5 Drawing Sheets

COMPOSITIONS AND METHODS FOR IMPROVING CARDIOVASCULAR HEALTH

BACKGROUND

1. Field of the Invention

The present invention generally relates to compositions and methods for improving cardiovascular health. In particular, to such compositions and methods comprising delivering a selection of amino acids, plant-derived stanols and sterols, isoflavones, and low glycemic carbohydrates and medium chain fatty acids to the elderly.

2. Description of the Related Art

As the population ages, and in particular as the "baby boomers" grow into their old age, the health problems associated with aging grow increasingly important. This is particularly true in a health system such as the current one where health care costs are distributed across the population; the increased prevalence of aging-related health problems will result in generally increased costs. In addition, reactive health care is more expensive than preventative health care; for example, fixing bones or replacing a hip after a fall by a frail patient is more expensive than preventing that fall by decreasing the patient's frailty. For these and other reasons, it is desirable to have effective, relatively inexpensive means for preventing and ameliorating health problems pervasive in the aged population.

Cardiovascular disease and its related complications, such as stroke and myocardial infarction, are believed to be the current number one cause of mortality within the United States. The development of cardiovascular disease is thought to be due to atherosclerotic plaque formation within both large and small blood vessels. Plaque formation is due to many influences, including increased plasma lipids such as low-density lipoproteins (LDL) cholesterol, very low-density lipoproteins (VLDL) cholesterol, and triglycerides (TG). Recently, the metabolic syndrome of combined hypertension, altered cholesterol, and insulin resistance has been recognized. Studies have shown that 20-30% percent of the United States population has this configuration of metabolic abnormalities.

High circulating levels of cholesterol, low density lipoprotein, and triglycerides, as well as elevated blood pressure, are all believed to be risk factors for development of cardiovascular disease. Increased liver fat is also related to these parameters. These risk factors are particularly prevalent in the elderly, including but not limited to individuals over 65 years of age. Over 40% of individuals over 65 years of age that are screened have been found to have elevated cholesterol levels, and high blood pressure is believed to occur in more than 65% of individuals over 65 and close to 80% of those over 75. Occurrence of elevated triglyceride concentrations in the elderly is equally common, and over 50% of the elderly have elevated liver fat. It is therefore desirable to address these prevalent and morbid health problems, in the elderly and in the general affiliated population.

Generally, lowering plasma levels of LDL cholesterol and TG via lifestyle and pharmacologic means has been positively associated with improvements in both morbidity and mortality from cardiovascular disease. Further, a lower fat diet with conversely more protein has been suggested to help prevent athlerosclerotic lesions. However, lifestyle modifications including low-fat diets in conjunction with moderate exercise appear to be difficult to maintain in the modern United States, and the majority of patients are unable to maintain lifestyle changes long-term. Pharmacologic means such as treatments with niacin, fibrates and statins have all been shown to be effective, but are not without side effects. For example, the facial flushing induced by niacin is a major limitation in its use; fibrates cause liver dysfunction and skin rash; and statins are increasingly associated with myopathy. Thus, therapeutic options that are effective, easy to maintain, and have minimal side-effects are desirable to properly address this epidemic of cardiovascular metabolic abnormality. Moreover, current treatment modalities focus on each of these risk factors independently. In order to minimize adverse interactions between treatment modalities and simplify treatment regimens to encourage patient compliance, it is desirable for one treatment to address multiple facets of cardiovascular health.

More specific aspects of current treatments also have room for improvement. Triglyceride metabolism is believed to involve multiple tissues within the body and has several aspects. Initially, fat is absorbed via the gut and secreted into the splanchnic bloodstream in the form of chylomicrons. Chylomicrons are high in TGs and have the apolipoproteins ApoB-48, ApoCII and ApoE. Chylomicrons are circulated to peripheral tissues, and the TGs are there broken down into free fatty acid (FFA) and glycerol via lipoprotein lipase (LPL). The chylomicron remnants have low levels of TG and increased concentrations of cholesterol, and are transported to the liver. Glycerol and FFA released by the lipoprotein lipase may also be absorbed by the liver. In the liver, TGs and FFAs have several fates. In the fasted state, they can be oxidized to produce ATP or released as an energy source for other tissues. Alternatively, in the fed state, Acyl-CoA can be reesterified into TGs, which are then either stored within hepatocytes, or secreted in the bloodstream alone or as part of VLDL. VLDL has ApoB-100 protein on the surface and once in circulation, VLDL gains the proteins ApoE and ApoCIII from HDL particles and travels to peripheral tissues, where, like chylomicron, TGs are extracted via lipoprotein lipase. As the TG concentration decreases and the cholesterol proportion increases, the lipids turn into LDL.

There are believed to be multiple sites of regulation of TG metabolism. ApoCIII has been shown to inhibit hepatic lipase and inhibit the interaction of TG with hepatic lipoprotein receptors. ApoCIII is thought to increase TG in the plasma of the blood by decreasing peripheral clearance via inhibition of LPL. ApoCII is believed to increase the peripheral clearance of TG's by simulating LPL. Both ApoCII and ApoCIII concentrations and synthetic rates have been closely tied to plasma TG concentrations in healthy patients and those with hyperlipidemia.

Several of these sites of regulation have been targeted by different drugs. Several drugs are currently used to block the initial absorption of TG and cholesterol via the gut, such as eztembamide. Nicotinic acid, or niacin, is believed to work via binding to HM74 receptors in adipose tissue, and via cAMP causes a reduced association of hormone sensitive lipase (HSL) with lipid droplets in adipose tissue, thus causing a decrease in FFA release from adipose tissue. Other drugs, such as the PPAR agonist fibrates, are thought to increase the oxidation of fats within mitochondria and peroxisomes, and thus decrease the hepatic output of TG. Further, they increase plasma clearance by increasing ApoCII expression and activity and decreasing the expression of ApoCIII. They also are believed to increase the expression of APoA, a protein specific to HDL, and thus have been demonstrated to induce moderate increases in HDL concentrations. Statins are believed to work by inhibiting HmgCoase within the liver, and decreasing the de novo synthesis of cholesterol.

Fibrates are believed to have a slightly greater efficacy in terms of lowering plasma TGs compared to statins, although the percent change depends on the population being treated. It has been shown, in elderly patients with normotryglyceridemia, that fenofibrate treatment decreased plasma TGs within 10 days of treatment. In patients with mixed hyperlipidemia, 80 mg of atorvostatin daily were shown to reduce TGs by 65% and VLDL by 57% whereas 200 mg of fenofibrate decreased TGs and VLDL by 57% and 64%, respectively. Patients with type 2 diabetes mellitus (T2DM) were shown to experience a 27% decrease in plasma TGs following 3 months of fenofibrate therapy. Adults with hypertryglyceridemia were shown to experience a 46% decrease in postparadial TGs after fenofibrate treatment. After treatment with the fibrate gemfibrozil, TG concentrations were shown to decrease by 38% in patients with isolated hypercholesterolemia and 45% in patients with hypertryglyceridemia and hypercholesterolemia; the maximal effects were seen within 4 weeks of treatments. Based on these studies, it appears that in patients with hypertryglyceridemia, the extent of decrease is greater than patients with normotryglyceridemia and can be expected to range from about 25-60%. The goal of a nutritional supplement is to achieve comparable or better results without negative side effects.

Figure 2:
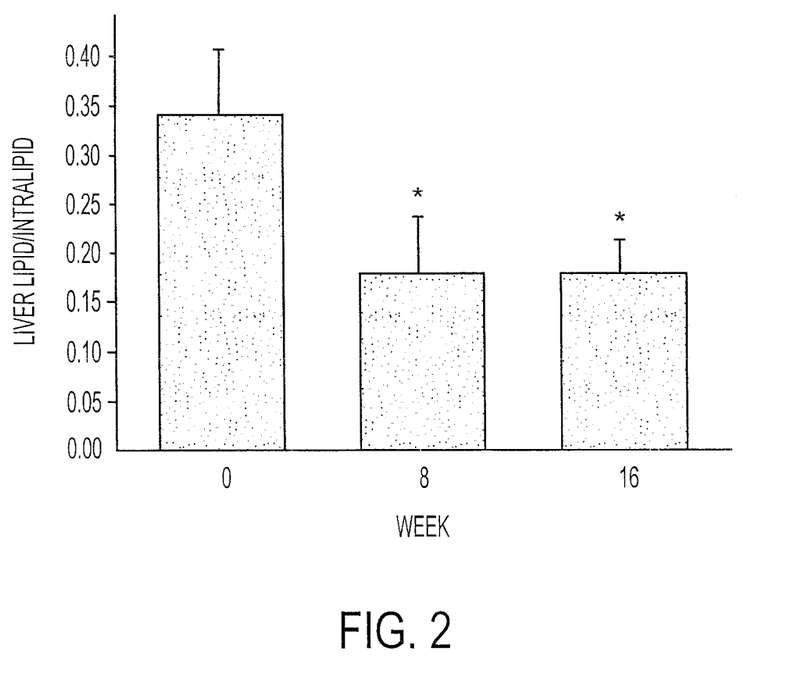
FIG. 2 shows a comparison of the effects of a composition of essential amino acids and arginine, compared to a fibrate drug.

Fibrate treatments including fenofibrate (a prescription drug) commonly induce the undesirable side effect of liver toxicity. It is therefore desirable to achieve similar or improved efficacy of fibrates without such side effects. The effects of a composition of essential amino acids (EAAs) (i.e., those that cannot be synthesized by the body) and arginine was compared to the effect of fenofibrate in a similar population of elderly. In contrast to the EAA+arginine, fenofibrate treatment for 60 days had no significant effect on liver triglyceride. Plasma triglyceride concentration fell approximately 33%, as compared to the 20% reduction in those receiving EAAs+arginine. These results are shown in FIG. 2. Due to these positive effects in the absence of negative side effects, it is desirable for a composition for improving cardiovascular health to comprise EEAs.

Alternatively or in addition to pharmaceutic interventions, isocaloric diets with excess protein may improve plasma TGs to the same extent as PPAR agonists and statins. A diet consisting of 22% protein was shown to significantly lower plasma TGs by 32% after 4 weeks, compared to a diet of 12% protein. When patients with T2DM switched 15-30% of their calories from carbohydrates to protein, fasted TG was shown to decrease by 22%, and post-parandial glucose decreased, but cholesterol levels did not change. Plasma TGs were reduced by 23±5% following a high protein diet in patients with pre-existing hypercholesterolemia. However, when elderly patients with poorly controlled T2DM ingested 8 g/day of a mix of 11 amino acids, they were shown to experience significant decreases in post-parandial glucose, hemoglobin A1C, insulin and insulin resistance, but had no changes in plasma lipid parameters. Patients with T2DM were instructed to follow a 30% protein diet rather than a 15% protein diet and at 8 weeks, and were found to have no changes in lipid measurements or glucose control. An epidemiological (rather than biochemical) study of protein intakes effect on cardiovascular health, the Nurses Health Study, tracked over 80,000 women aged 34 to 59 years for 14 years and showed a moderate correlation between the level of protein intake and the occurrence of ischemic heart disease. Data also indicates that higher levels of protein intake have protective effects on elevated blood pressure. A variety of epidemiological studies indicate an inverse relationship between protein intake and blood pressure. It is therefore desirable for a composition for improving cardiovascular health to increase the patient's protein intake.

Figure 1:
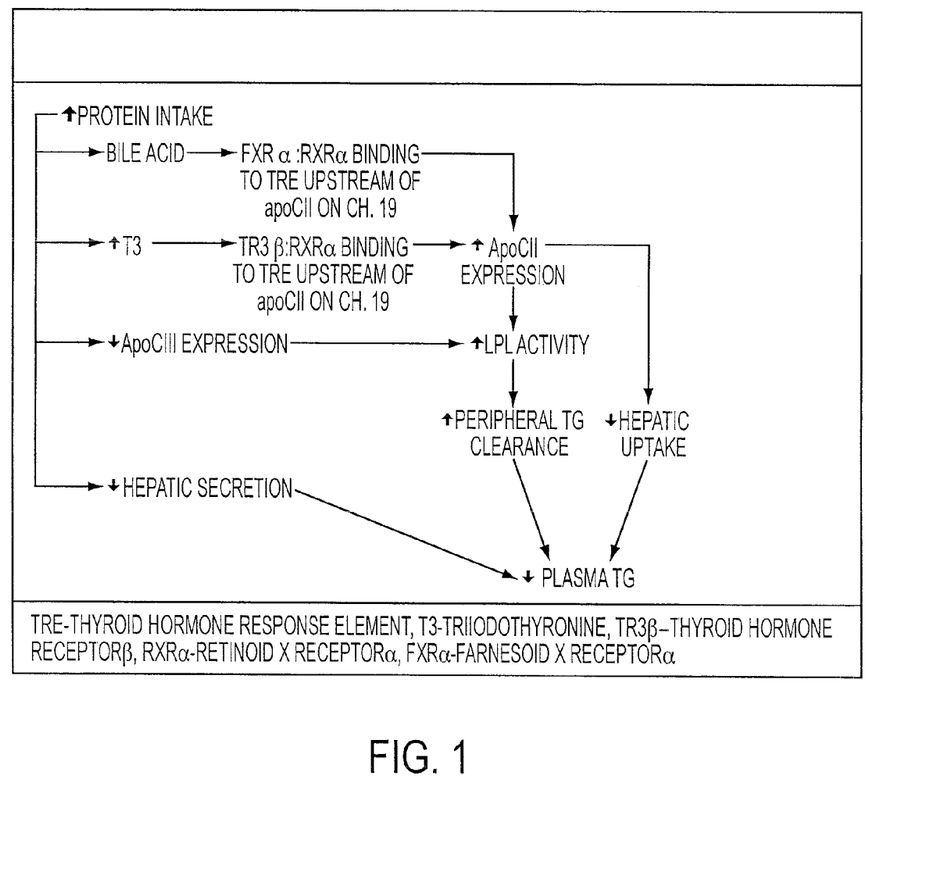
FIG. 1 shows what is believed to be the mechanism of dietary protein decreasing plasma triglycerides.

The mechanism by which protein alters plasma triglyceride concentrations is unclear. Current theories are shown in FIG. 1. It is believed to take approximately 3 weeks for plasma lipids to be altered following the initiation of a high protein diet. LPL is believed to be crucial to the regulation of plasma triglyceride, and may be altered by activity levels and diet. A diet high in fats and/or saturated fat is believed to depress LPL activity in adipose tissue and increase LPL activity in muscle tissue. Exercise has also been show to increase LPL activity. ApoCII transcription is believed to be regulated by PPAR-α and thyroid response element gene domains on chromosome 19. These genes are believed to be stimulated by alteration in bile acids (including chenodeoxycholic, deoxycholic, and lithocolic acid concentrations) PPAR-α agonists, and thyroid hormone, and down-regulated by human ApoA-1 regulatory protein. Current medications that stimulate the thyroid response element (TRE) are believed to significantly lower plasma TG and cholesterol in rats. Protein likely does not alter the gut absorption of triglyceride, since the effects of a high protein diet are believed to be additive to those of the fat binding resin cholestyramine. It may also be that protein supplementation alters the secretion of TGs from the liver, although the likely mechanism may be the reduction of carbohydrates in the diet. A high protein diet in Zucker rats decreased hepatic VLDL secretion, although so does a high fat diet. Obese Zucker rats had a several fold increase in the incorporation of both protein and palmitate into VLDL particles, indicating that the synthetic function of both were increased in obesity. A diet high in carbohydrate increases plasma levels of ApoCIII, leading to decreased plasma TG clearance. A high carbohydrate diet also increases ApoCII concentrations, and thus alters the ratio between the ApoCIII and ApoCII.

The mechanism responsible for an effect of protein intake on lowering blood pressure is believed to be at least in part due to the extra intake of arginine. Blood pressure is influenced by the diameter of blood vessels, which is partially controlled by nitric oxide (NO). Substances that can alter the production of NO have been shown to lower blood pressure. Arginine supplementation enhances NO synthesis, reduced oxidative stress and modulation of renal hemodynamics, among others. When arginine is administered to hypertensive or healthy humans, in causes vasodilatation and decreased blood pressure. It is therefore desirable for a composition to improve cardiovascular health to include arginine, in order to decrease blood pressure.

This decrease in plasma lipids profiles associated with a high protein diet may be due to the decreased content of carbohydrate. 3 weeks of a diet high in carbohydrates rather than fat induced significant increases in plasma TG, due to increased hepatic de novo synthesis of TG. The increase in plasma TG following a high carbohydrate diet is rapid, with changes seen with 4 days of diet alteration. Further, plasma TG decreased after either a high fat or a high protein diet, as compared to a high carbohydrate diet. This substitution of substrate source is not restricted to dietary substitution: peritoneal dialysis patients receiving a 1.1% solution of amino acids instead of all glucose were shown to experience a 13% decrease in plasma TGs within 1 month of the solution change. Other studies have found similar results over 3 years of treatment.

Because carbohydrate intake is thus believed to induce increases in blood lipids in individuals with preexistent elevations, it is desirable for a composition for improving cardiovascular health to have minimal carbohydrates. This is especially desirable for elderly individuals who are often insulin resistant and cannot obtain nutrition from carbohydrates. Medium chain triglycerides are believed to be particularly suitable for this purpose, as they can be readily oxidized for energy and do not require the hormone insulin to be taken up by tissues. Long chain fatty acids commonly found in food require an enzyme system (carnitinepalmitoyltransferase) to transport the fatty acid into the mitochondria for oxidation. Medium chain triglycerides bypass this step because medium chain fatty acids can diffuse directly into the mitochondria. Therefore, such medium chain fatty acids can provide energy without the concomitant detrimental effect on blood lipids induced by carbohydrate intake. This is of benefit to individuals such as the elderly with insulin resistance, since insulin sensitivity is not required for metabolism of medium chain triglycerides.

The mechanism by which carbohydrate levels influence cardiovascular health remains under study. Carbohydrate intake stimulates ApoA-1, which may play a role in the appearance of increased TG following a high carbohydrate diet. Diets high in carbohydrate are believed to increase the proportion of bile cholesterol, and disrupt the balance between bile acids and cholesterol.

Increasing the proportion of plant sterols in the diet also has been associated with decreased cardiovascular disease. Plant sterols, or phytosterols, are found in cellular membranes of numerous plants, and include steroids with a hydroxyl group in the three-position of the A-ring. Sterols are long chain fatty acid esters and are believed to bind cholesterol in the gut effectively in the gut and prevent its absorption. The three sterols believed to be the most effective in lowering plasma cholesterol are B-sitosterol, campesterol, and stigmasterol. A meta-analysis of multiple studies with plant sterols found that chronic consumption decreased LDL by approximately 0.33-0.50 mmol/L, or a 8-13% decrease, and that this decrease is the equivalent of a 20-25% decrease in cardiovascular disease. Dose response curves appear to be linear, with the minimal effective dose of 1.5 g a day inducing a 10% decrease in total cholesterol. Based on such findings, the National Cholesterol Education Program Adult Treatment Panel has recommended a trial of 2 g a day of plant sterols in patients with hypercholesterolemia, prior to initiation of medical treatment.

Figure 3:
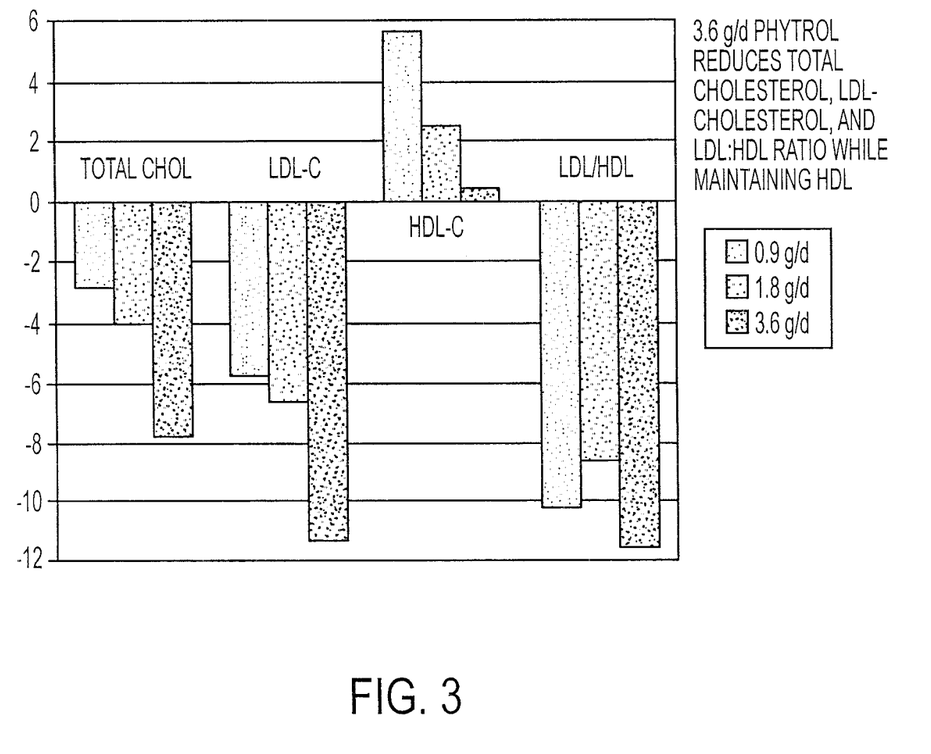
FIG. 3 shows the effect of phytostenols on blood lipids.

Plant sterols are thought to work by decreasing intestinal cholesterol absorption. Plant sterols have been shown to be as effective in lowering cholesterol as starting doses of first generation statins. FIG. 3 shows the response of blood lipids to various doses of phytosterols (e.g., PHYTROL® (a cholesterol-lowering agent). Importantly, the effect of phytosterols is believed to be pronounced on cholesterol, which the EAA+arginine mixture did not significantly affect. On the other hand, phytosterols are not believed to affect plasma triglycerides, which EAAs+arginine is believed to do. It is therefore desirable for a combination to lower cholesterol, the LDL/HDL ratio, triglycerides, and liver triglyceride, as a combination of EAA+arginine and phytosterols is believed to do.

A ratio of sterols to stanols have been shown to lower LDL while raising HDL more effectively than stanols alone, due to the stanols' shorter chain lengths. A sterols to stanols ratio of 2:1 yields more effective cholesterol lowering (up to 8% greater). Additionally, the balanced use of sterols and stanols presents a more functional ingredient which is less waxing and able to be used in non-fat food matrices.

Figure 4:
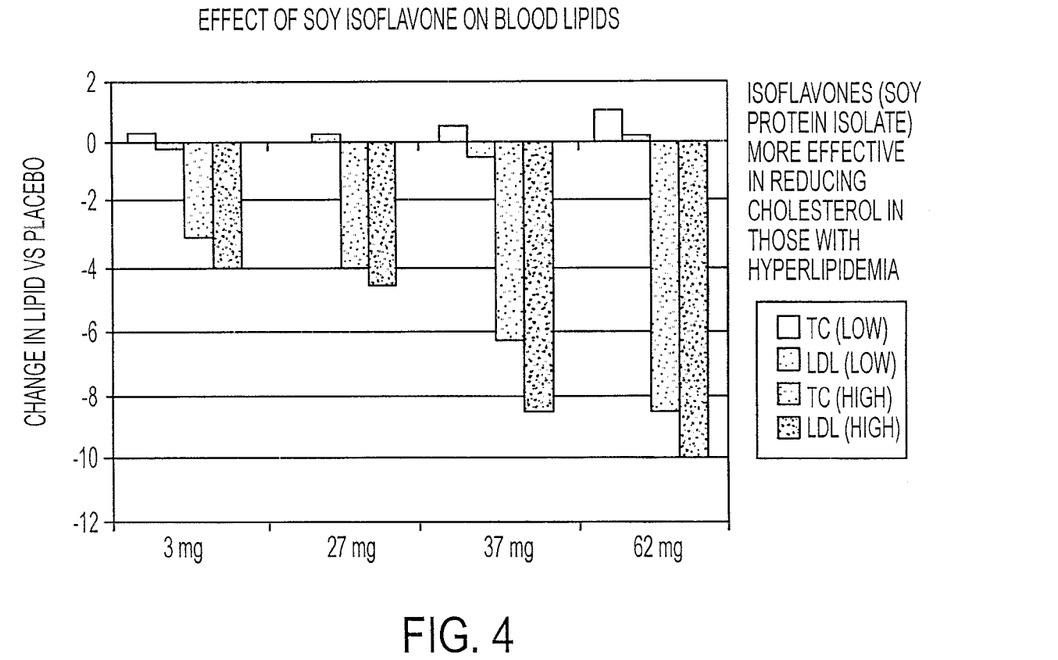
FIG. 4 shows the effect of isoflavones on blood lipids.

In a manner similar to phytosterols, isoflavones decrease total cholesterol as well as LDL cholesterol. Isoflavones may also be referred to as 3-phenyl-4H-1-benzopyr-4-one, and may have added functional groups. As in the case of the EAAs+arginine, the effect of isoflavones is greater in those with initially elevated values. This is shown in FIG. 4. It is therefore desirable for a composition for improving cardiovascular health to comprise isoflavones.

SUMMARY

Because of these and other problems in the art, disclosed herein is, among other things, a composition of matter for improving cardiovascular health comprising amino acids, a phytostenol, a stanol, and a isoflavone; wherein said amino acids are selected from the group of histidine, isoleucine, leucine, valine, lysine, methionine, phenylalanine, threonine, arginine, and citrullene.

In an embodiment, the composition may further comprise a low glycemic carbohydrate. In an alternative or further embodiment, the composition may further comprise a medium chain fatty acid.

In an embodiment of the composition, said amino acids have a combined mass of about 11 grams; and said amino acids further comprise about 0.36 g histidine, about 0.94 g isoleucine, about 3.95 g leucine, about 1.88 g lysine, about 0.39 g methionine, about 0.51 g phenylalanine, about 1.05 g threonine, about 0.82 g valine, and about 1.10 g arginine. In a further embodiment, said phytostenol and said stanol are in a balanced ratio. Said isoflavone may have a combined mass of about 30 to about 40 g. In a further embodiment, the composition may further comprise a low glycemic carbohydrate, wherein said low glycemic carbohydrate has a combined mass of about 0.01 to about 15 g. The composition may also or further comprise a medium chain fatty acid, wherein said medium chain fatty acid has a combined mass of about 0.01 to about 15 g.

In embodiments of the composition, the composition may further comprise supplemental minerals, vitamins, and/or an excipient.

Also disclosed herein is a method of improving cardiovascular health comprising having a patient; and delivering to said patient a composition of matter for improving cardiovascular health comprising amino acids, a phytostenol, a stanol, and a isoflavone; wherein said amino acids are selected from the group of histidine, isoleucine, leucine, valine, lysine, methionine, phenylalanine, threonine, arginine, and citrullene.

In an embodiment of the method, said composition further comprises a low glycemic carbohydrate. In an alternative or further embodiment, said composition further comprises a medium chain fatty acid.

In an alternative or further embodiment, said amino acids have a combined mass of about 11 grams; and said amino acids further comprise about 0.36 g histidine, about 0.94 g isoleucine, about 3.95 g leucine, about 1.88 g lysine, about 0.39 g methionine, about 0.51 g phenylalanine, about 1.05 g threonine, about 0.82 g valine, and about 1.10 g arginine. In a further embodiment, said phytostenol and said stanol are in a balanced ratio. In a further or alternative embodiment, said isoflavone has a combined mass of about 30 to about 40 g. In a further or alternative embodiment, said delivering further comprises delivering said composition orally to said patient twice daily. Said patient may be over sixty-five years of age.

Also disclosed herein is a method of increasing muscle mass, strength, and functional performance, comprising having a patient; and delivering to said patient means for improving cardiovascular health by delivering amino acids, a phytostenol, a stanol, and a isoflavone; wherein said amino acids are selected from the group of histidine, isoleucine, leucine, valine, lysine, methionine, phenylalanine, threonine, arginine, and citrullene.

In a further embodiment of the method, said delivering further comprises delivering a low glycemic carbohydrate. In an alternative or further embodiment, said delivering further comprises delivering a medium chain fatty acid. In an alternative or further embodiment, said delivering is oral. Said patient may be over sixty-five years of age.

DESCRIPTION OF PREFERRED EMBODIMENTS

The compositions and methods described herein comprise a blend of components that cooperate improve blood pressure and lower plasma concentrations of total cholesterol, LDL cholesterol, and triglycerides, and liver fat and so together have a beneficial effect on cardiovascular health. Also disclosed herein are modes of delivering such a composition in order to improve cardiovascular health. In a preferred embodiment, the compositions and delivery methods improve the cardiovascular health of the elderly, including but not limited to those individuals over 65 years old.

The composition may comprise amino acids, plant stanols and sterols, isoflavones, and low glycemic carbohydrates and medium chain fatty acids.

It is believed that only the essential amino acids (EAAs) and arginine are needed to elicit the TG lowering effect that can be induced by a high protein diet. It is contemplated that additional amino acids may be desirable to accomplish other purposes such as remedying individual deficiencies or addressing other health problems.

Further, it is also believed that the effect of the amino acid component of the compositions disclosed herein can be elicited in the absence of any other dietary changes, making EAA delivery a simple means for improving cardiovascular health without major lifestyle changes. EAAs may reduce circulating and tissue TG concentrations and improve insulin sensitivity in subjects with impaired glucose tolerance, including elderly subjects. EAAs may also improve cardiovascular health without the undesirable side effects of pharmaceutical interventions, e.g. fibrates. Some positive effects of a composition comprising EAAs on cardiovascular health are shown in FIG. 2.

In an embodiment, the composition comprises the essential amino acids (meaning that they are not produced in the body), including histidine, isoleucine, leucine, valine, lysine, methionine, phenylalanine, and threonine. The amino acid arginine and/or its immediate precursor citrulline may be included in order to have a further effect of lowering blood pressure. The amino acids may be in free form or contained in intact protein, including whey protein or peptides. The amino acids may be in the 1-form.

In a preferred embodiment, the composition further comprises phytosterols and stanols, more preferably in a balanced blend, and most preferably in a 2:1 ratio of sterols to stanols. These may be included in order to capture the believed effect of these esters in lowering LDL and decreasing cardiovascular disease, which is believed to be superior to a simple EAA+arginine mixture. In a further embodiment, the composition comprises B-sitosterol, campesterol, stigmasterol, and/or their functional equivalents.

In an embodiment, the composition comprises isoflavones, in order to capture the believed effect of decreasing total cholesterol as well as LDL cholesterol shown in FIG. 4. In a further embodiment, the isoflavone may be derived from soy or other functionally equivalent sources.

In an embodiment, the composition comprises low glycemic carbohydrates. The low glycemic carbohydrate may provide energy while still accomplishing the decrease in plasma lipids profiles believed to be associated with a diet with decreased carbohydrates. In addition, the low glycemic carbohydrate may provide energy without eliciting a significant insulin response. The elderly are generally resistant to the action of insulin, so avoiding the insulin response will be advantageous to that population. The low glycemic carbohydrate may also be useful in improving the taste of the composition, making it a more palatable means for improving cardiovascular health and so improving patient compliance.

In an embodiment, the composition's principal energy substrate may be medium chain triglycerides. One example of such a medium chain triglyceride may be triolein, which consists of three molecules of oleic acid bound together by a backbone of glycerol. As explained above, such medium chain fatty acids can provide energy without the concomitant detrimental effect on blood lipids induced by carbohydrate intake. This is of benefit to individuals such as the elderly with insulin resistance, since insulin sensitivity is not required for metabolism of medium chain triglycerides. In an embodiment, a certain amount of carbohydrate may be required from the standpoint of nutrient production (i.e., taste and constituency), but it will remain a minor contributor to the overall energy content of the composition.

In an embodiment, a dose of a composition disclosed herein comprises at least about 11 g of amino acids. In a further embodiment, those amino acids comprise about 0.36 g histidine, about 0.94 g isoleucine, about 3.95 g leucine, about 1.88 g lysine, about 0.39 g methionine, about 0.51 g phenylalanine, about 1.05 g threonine, about 0.82 g valine, and about 1.10 g arginine. Any proportion, quantity, and selection of EAAs that improves cardiovascular health is contemplated. The amino acids may be in the form of free amino acids, peptides, or intact protein.

In a further embodiment of a composition dose of at least about 11 g of amino acids, the composition may contain about 2 g of phytosterols, which may compromise B-sitosterol, campesterol, stigmasterol, their functional equivalents, and any combination thereof. In a further or alternative embodiment, the composition may contain about 30-40 mg of isoflavones, which may be derived from soy or any other functionally equivalent source.

The composition may contain between about 0-15 g low glycemic carbohydrates and/or about 0-15 g medium chain triglycerides. The proportions disclosed herein are scalable and alterable so long as it improves cardiovascular health.

The compositions may also optionally comprise vitamins. The vitamins may be fat-soluble or water soluble vitamins. Suitable vitamins include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The compositions may also comprise at least one excipient. Non-limiting examples of suitable excipients include a buffering agent, a preservative, a stabilizer, a binder, a compaction agent, a lubricant, a dispersion enhancer, a disintegration agent, a flavoring agent, a sweetener, a coloring agent, and combinations of any of these agents.

In one embodiment, the excipient is a buffering agent. Non-limiting examples of suitable buffering agents include sodium citrate, magnesium carbonate, magnesium bicarbonate, calcium carbonate, and calcium bicarbonate.

The excipient may comprise a preservative. Suitable examples of preservatives include antioxidants, such as alpha-tocopherol or ascorbate, and antimicrobials, such as parabens, chlorobutanol, or phenol.

In another embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In yet another embodiment, the excipient may be a disintegrant. The disintegrant may be a non-effervescent disintegrant. Suitable examples of non-effervescent disintegrants include starches such as corn starch, potato starch, and pregelatinized and modified starches thereof; sweeteners, clays such as bentonite, micro-crystalline cellulose, alginates, sodium starch glycolate, gums such as agar, guar, locust bean, karaya, pecitin, and tragacanth. The disintegrant may be an effervescent disintegrant. Suitable effervescent disintegrants include sodium bicarbonate in combination with citric acid, and sodium bicarbonate in combination with tartaric acid.

The excipient may include a flavoring agent. Flavoring agents incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chioro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. The choice of sweetener may be directed by the insulin resistance of the patient.

Depending upon the embodiment, it may be desirable to provide a coloring agent in the composition's outer layer. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The weight fraction of the excipient or combination of excipients in the formulation may be about 30% or less, about 25% or less, about 20% or less, about 15% or less, about 10% or less, about 5% or less, about 2%, or about 1% or less of the total weight of the amino acid composition.

Also disclosed herein are methods of delivering a composition or means for improving cardiovascular health, including but not limited to dosage. The compositions disclosed or made obvious herein may be formulated into a variety of forms and administered by a number of different means. The compositions may be administered orally, rectally, or parenterally, in formulations containing conventionally acceptable carriers, adjuvants, and vehicles as desired. The term "parenteral" as used herein includes subcutaneous, intravenous, intramuscular, or intrasternal injection, or infusion techniques. In an exemplary embodiment, the disclosed compounds are administered orally.

Solid dosage forms for oral administration may include capsules, tablets, caplets, pills, troches, lozenges, powders, and granules. A capsule typically comprises a core material comprising a disclosed composition and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

Alternatively, powders or granules embodying the compositions disclosed and made obvious herein may be incorporated into a food product. The food product may be a drink. Non-limiting examples of a suitable drink include fruit juice, a fruit drink, an artificially flavored drink, an artificially sweetened drink, a carbonated beverage, a sports drink, a liquid diary product, a shake, and so forth. The food product may also be a solid foodstuff. Suitable examples of a solid foodstuff include a food bar, a snack bar, a cookie, a brownie, a muffin, a cracker, an ice cream bar, a frozen yogurt bar, and the like.

The compositions may also be in liquid dosage forms for oral administration. Liquid dosage forms include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents.

The disclosed compositions may be utilized in methods to improve cardiovascular health. In an embodiment, the method comprises administering the composition as described above twice per day between meals. The amount per dose may be about 10, 11, 12, 13, 14, 15, 16, 17, 18, 19, 20, 21, 22, 23, 24, 25, 26, 27, 28, 29, or 30 g. Alternatively, the composition may be administered one day per day, three times per day, or four times per day.

In an alternative or further embodiment of a method of delivery, the composition may also be used in conjunction with exercise. For example, the composition may given before or immediately after exercise.

The following example provides embodiments of compositions, methods, their use, and the effects of such use.

Example 1

The aim of the study was to investigate the effect of supplementation of the diet with EAA+arginine on plasma, liver and muscle lipids in elderly individuals.

Twelve elderly volunteers participated in a 16 week study period. They ingested 11 g of EAA+arginine two times a day, between meals. Diet and activity were not otherwise modified, Every 4th week body composition was measured by a full-body dual-energy x-ray absorptiometry (DEXA) scan. In addition, a plasma lipid panel was determined. Muscle and liver lipids were measured by magnetic resonance spectroscopy (MRS) every 8th week. At weeks 0 and 16, a muscle biopsy was also collected from m. vastus lateralis for measurement of activities of oxidative enzymes.

Twelve elderly individuals (7 females, 5 males, 67.0±5.6 (SD) years, 74.3±19.7 kg at baseline) participated in the study. They were fully informed about the purpose and procedures of the study before written consent was obtained. Each subject had a complete medical screening prior to participation in the experiments (51±9 days before start of supplementation), including vital signs, blood tests, urine tests, and a 12-lead electrocardiogram. Exclusion criteria included evidence for heart disease, hyperlipidemia, kidney or liver disease, or any other disease that might influence the results of the study. The subjects also underwent a standard oral glucose tolerance test (OGTT) using 75 g of dextrose. Only subjects with impaired glucose tolerance defined as a plasma glucose concentration >180 mg/dl at 1 hr or >140 mg/dl at 2 hr after oral intake of 75 g glucose, were included. Diabetic subjects (plasma glucose concentration >200 mg/dl at 1 hr or 2 hr after glucose intake) with a reduced insulin production, and subjects taking any medication to treat abnormal blood lipid levels, were not included in the study.

Each dose of the nutritional supplement consisted of 11 g of amino acids with the following composition: 0.36 g histidine, 0.94 g isoleucine, 3.95 g leucine, 1.88 g lysine, 0.39 g methionine, 0.51 g phenylalanine, 1.05 g threonine, 0.82 g valine, 1.10 g arginine. This was taken in two daily doses in the form of capsules, and recorded in a diary. The first dose was taken between breakfast and lunch, and the second dose was ingested between lunch and dinner. The subjects visited the hospital every two weeks to pick up a new supply of supplements. In the weeks with no hospital visits, the subjects were given follow-up calls to check on the intake of the supplements, as well as on diet, activity and anything else (sickness, etc.) that might influence the results of the study.

Before the start of the study the subjects were counseled to maintain their typical dietary intake and physical activity pattern. During their visits to the hospital and in telephone calls between visits, they were asked about this and reminded to not make any changes. The Physical Activity Scale for Elderly (PASE) was used to measure their physical activity during the study period. Further, at the start of the study the subjects were instructed by the dietician at the GCRC on how to complete a diet diary. In the week before the first overnight stay and every 4th week thereafter (week 3, 7, 11, and 15), the participants recorded their diet for 3 days (two week-days and one weekend-day).

Every 8th week, the intramuscular lipid concentration of m. soleus was measured with a $^1$H knee coil on a GE Advantage 1.5 Tesla whole-body imager (General Electric, Milwaukee, Wis.). The widest part of the calf was located during the first study, and measured from the floor and marked. A marker was placed at the location during the scan, and this slice of leg was always used for scans. Four areas were selected from the coronal slice localizer and were traced onto a transparency along with multiple anatomic landmarks. These four areas were then rescanned during each subsequent MRS analysis. A tube of 20% INTRALIPID® (i.e, high-fat total parenteral feeding solution; Baxter Healthcare, Deerfield Park, Ill.) was placed inside the knee coil to obtain a standard external reference. After a preliminary localization image, three to seven voxels (7 mm×7 mm×10 mm each) were chosen in m. soleus free from fascia, gross fat marbling, and vessels. The exact voxel volumes were recorded. A voxel was also chosen from the INTRALIPID® external reference. An optimized PRESS (Point RESolved Spectroscopy) sequence with a repetition time of 2000 ms and an echo time of 35 ms was run. Peak positions and areas of interest [extramuscular $(CH_2)$, intramuscular $(CH_2)$, extramuscular $CH_3$, intramuscular $CH_3$, total creatine, and trimethylamines] were determined by time domain fitting using jMRUi. In brief, all water-suppressed free induction decay (FID) (metabolite FID) were deconvoluted with the water-unsuppressed FID (water FID) acquired from the same voxel to correct for zero-order phasing and removal of eddy current-induced artifacts. The resulting metabolite FIDs were analyzed with AMARES (Method of Accurate, Robust and Efficient Spectral fitting), a nonlinear least-square-fitting algorithm operating in the time domain.

Spectra from voxels, which did not have optimal shimming or clear intracellular and extracellular lipid peak resolution, were not used in the AMARES fitting analysis. This process was repeated for the INTRALIPID® phantom. The TG levels were computed as a ratio relative to the Intralipid standard using the following formula: TG=[(PM/VM)/(PI/VI)], where PM is the methylene peak area, VM is the total measured tissue voxel volume, PI is the INTRALIPID® peak area, and VI is the INTRALIPID® voxel volume. This measurement is a TG concentration normalized to INTRALIPID® concentration, and thus it is unitless.

Liver lipid concentration was measured with a $^1$H whole-body coil on the same system. Hepatic measurements were performed in the middle right lobe. The scans were localized to the same area of the liver via anatomic landmarking of the hepatic blood flow and the ribs, so that approximately the same area of liver was scanned with each study. A tube of INTRALIPID® was again used for reference. After a preliminary localization scan, a voxel (~30 mm×30 mm×20 mm) was chosen at a location free from large vessels. An optimized PRESS sequence was run 256 times without respiratory gating. These spectra represent an average lipid concentration measurement over the mid-right lobe because respiratory gating was not conducted. By placing the subjects prone, using light restraints, and coaching shallow breathing, the movement induced by respiration was reduced. Spectra were manually phased, and final analysis was then performed with jMRUI.

The subjects underwent a full-body DEXA scan every $4^{th}$ week to determine body composition. All DEXA scans were performed on a Hologic QDR 4500 A system (Hologic, Inc., Bedford, Mass.).

Plasma glucose concentration was determined enzymatically (YSI 1500, Yellowspring Instruments, Yellowspring, Ohio, USA). Plasma insulin concentration was determined by a radioimmunoassay method (Diagnostic Products Corporation, Los Angeles, Calif., USA). Plasma amino acid concentrations were analyzed by high-performance liquid chromatography (Waters Alliance HPLC System 2690, Milford, Mass.). Enzymatic methods were used to determine plasma FFA (NEFA-C, Wako Chemicals GmbH, Neuss, Germany) and glycerol (Sigma-Aldrich, St. Louis, Mo.) concentrations. The lipid panel was comprised of triglycerides (TG), total cholesterol, and HDL-cholesterol concentrations. They were all measured on a Vitros 950 system (Ortho-Clinical Diagnostics, Raritan, N.J.). The HDL-cholesterol was measured by precipitation of the LDL and VLDL, and the cholesterol left in the supernatant (HDL) was then determined. The LDL-cholesterol (mgdl) was calculated using the Friedewald equation (LDL-cholesterol=Total cholesterol−HDL-cholesterol−Triglyceride/5). Thus, the quotient ([TG]/5) is used as an estimate of VLDL-cholesterol concentration.

Overall significance of differences in response of diet intake, ISI, tissue lipids, and fasting plasma lipids, insulin, and glucose concentrations with time was tested by one-way repeated measures analysis of variance (ANOVA) followed by Dunnett's test with week 0 as control (SigmaStat 2.03, SPSS Inc., Chicago, Ill.). The correlation between plasma TG concentrations at week 0 and changes in plasma TG concentration during the supplementation period was measured by Spearman rank correlation coefficient, whereas the corresponding correlation for liver lipid content was determined by linear regression analysis. Changes in amino acid concentration or muscle oxidative enzymes from week 0 to 16 were tested by paired t-tests. Comparisons of plasma lipid concentrations and ISI at screening (week 7) and week 0 were also done by paired t-tests. Results were considered significant if $P<0.05$. The results are presented as means±SE unless otherwise noted.

The amino acid supplementation was well tolerated by the subjects, and there were no overall changes in physical activity or diet during the study period. The dietary intake was 1733±226 kcal/day when no supplement was taken vs. an average of 1735±176 kcal/day during the supplementation period (n=9). Corresponding values for protein intake were 72.5±10.6 vs. 68.9±8.5 g/day (with vs. without supplement); fat intake was 64.3±12.2 vs. 63.1±6.5 g/day, and carbohydrate intake was 205.6±30.2 vs. 212.6±27.5 g/day.

The amino acid supplementation did not lead to changes in overall body mass (week 0 vs. 16: 74.31±5.67 vs. 74.60±5.62 kg), total fat mass (24.19±3.59 vs. 23.90±3.70 kg), or trunk fat mass (11.89±1.76 vs. 11.67±1.78). Plasma AA concentration did not change during the study.

There were no changes in plasma lipid concentrations from the screening time point until the start of the supplementation period (51±9 days without supplementation; Table 1).

Table 1 follows, and shows plasma lipid concentrations in IGT elderly (n=12) at baseline, and after 4, 8, 12, and 16 weeks of amino acid supplementation. The data are mean±SE. †ANOVA: $P<0.001$; ‡ANOVA: $P<0.05$; *$P<0.05$ vs. week 0.

TABLE 1

|  | Screening (~week −7) | Week 0 | Week 4 | Week 8 | Week 12 | Week 16 |
| --- | --- | --- | --- | --- | --- | --- |
| Triglycerides (mg/dl)† | 127 ± 14 | 128 ± 16 | 105 ± 11* | 112 ± 15* | 107 ± 13* | 102 ± 14* |
| Total cholesterol (mg/dl)‡ | 199 ± 11 | 200 ± 11 | 199 ± 11 | 188 ± 11 | 190 ± 9 | 186 ± 12 |
| HDL-cholesterol (mg/dl) | 57 ± 6 | 58 ± 6 | 62 ± 7 | 55 ± 5 | 56 ± 6 | 60 ± 6 |
| LDL-cholesterol (mg/dl) | 116 ± 7 | 116 ± 8 | 117 ± 8 | 110 ± 8 | 113 ± 7 | 106 ± 8 |
| VLDL-cholesterol (mg/dl)† | 25 ± 3 | 26 ± 4 | 22 ± 3* | 23 ± 3* | 21 ± 2* | 21 ± 3* |
| FFA (mEq/l) | — | 0.76 ± 0.06 | 0.60 ± 0.06 | 0.64 ± 0.05 | 0.62 ± 0.05 | 0.66 ± 0.04 |

Significant decreases were found in plasma TG (P<0.001), total cholesterol (P=0.048) and VLDL-cholesterol (P<0.001) concentrations during the study (Table 1). For TG and VLDL-cholesterol the changes from baseline were significant at all time points, whereas they did not reach significance at any specific time point for total cholesterol concentration.

Figure 5:
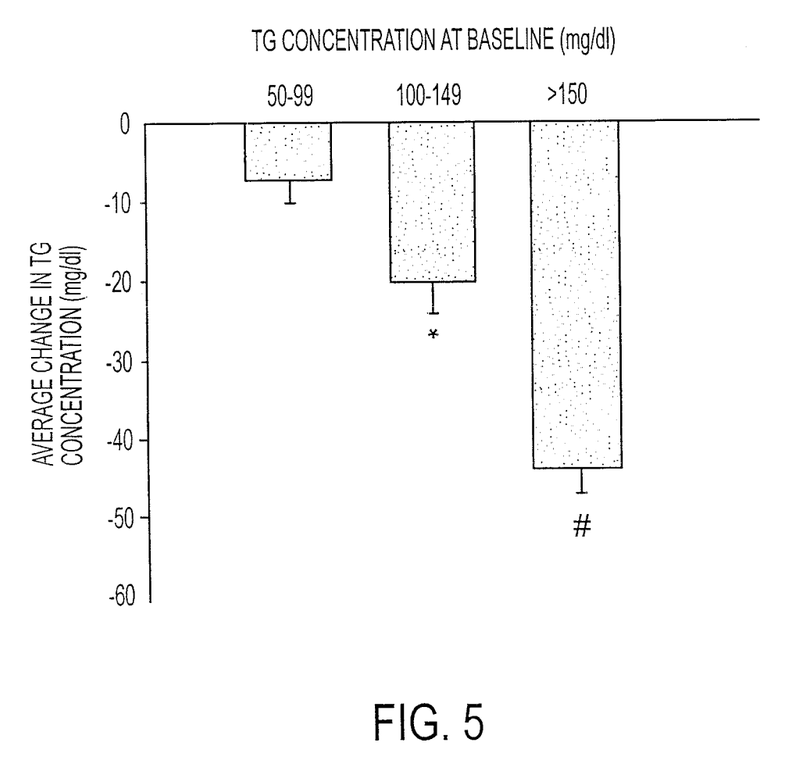
FIG. 5 shows average triglyceride concentration in response to delivery of a composition for improving cardiovascular health.

The changes in plasma TG concentrations during the study were related to starting level, with the greatest decrease in the subjects that initially had the highest plasma TG concentrations (FIG. 5). As FIG. 5 shows, the average plasma triglyceride concentration changes from baseline during 16 weeks of amino acid supplementation in elderly that had baseline values between 50-99 mg/dl (left; n=4), between 100-149 mg/dl (middle; n=5); and >150 mg/dl (right; n=3). The normal reference range is 30-170 mg/dl. Data are mean±SE; *P=0.01 vs. zero; #P=0.004 vs. zero.

The correlation was not linear, therefore we calculated the Spearman rank correlation coefficient, which was r=−0.828 between the starting value and the average change from baseline at 4, 8, 12 and 16 weeks (P<0.001). Most of the concentration changes occurred somewhere between 0-4 weeks (Table 1). Spearman rank correlation coefficient between the start value and the change from 0-4 weeks was −0.872 (P<0.001).

No changes were found in plasma FFA, and LDL- and HDL-cholesterol concentrations during the study (Table 1).

At the start of the study, there was a linear correlation between liver fat content and plasma TG concentration (r=0.85; P=0.007). Amino acid supplementation caused the liver fat content (liver TG/INTRALIPID® standard) to drop about 50% from the initial value of 0.34±0.06 at week 0 (P=0.021; n=8 at week 0 and 16, n=6 at week 8; FIG. 2). FIG. 2 shows liver lipids (liver TG/INTRALIPID® standard) at baseline, and after 8 and 16 weeks of amino acid supplementation (mean±SE; n=8 at week– and 16, n=6 at week 8); *P<0.05 vs. baseline. The change in liver fat content was most dramatic for the subjects starting out with the highest level (r=−0.86; P=0006). No significant changes were observed in intramuscular fat content.

The invention claimed is:

1. A composition of matter for improving cardiovascular health comprising:
   an amino acid blend, the blend comprising:
      about 0.36 g histidine; about 0.94 g isoleucine; about 3.95 g leucine; about 1.88 g lysine; about 0.39 g methionine; about 0.51 g phenylalanine; about 1.05 g threonine; about 0.82 g valine; and about 1.10 g arginine; and
   at least one selected from the group consisting of:
   citrulline;
   a phytostenol,
   a stanol, and
   a isoflavone.

2. The composition of claim 1 further comprising a low glycemic carbohydrate.

3. The composition of claim 1 further comprising a medium chain fatty acid.

4. The composition of claim 1 wherein said phytostenol and said stanol are in a 2:1 ratio.

5. The composition of claim 1 wherein said isoflavone has a combined mass of about 30 to about 40 g.

6. The composition of claim 2 wherein said low glycemic carbohydrate has a combined mass of about 0.01 to about 15 g.

7. The composition of claim 3 wherein said medium chain fatty acid has a combined mass of about 0.01 to about 15 g.

8. The composition of claim 1 further comprising supplemental minerals.

9. The composition of claim 1 further comprising vitamins.

10. The composition of claim 1 further comprising an excipient.

11. A composition of matter for the reduction of liver fat, the composition consisting essentially of:
   about 0.36 g histidine; about 0.94 g isoleucine; about 3.95 g leucine; about 1.88 g lysine; about 0.39 g methionine; about 0.51 g phenylalanine; about 1.05 g threonine; about 0.82 g valine; and about 1.10 g arginine.

* * * * *